United States Patent
Cho et al.

(10) Patent No.: US 8,883,134 B2
(45) Date of Patent: Nov. 11, 2014

(54) HUMAN INTERLEUKIN-1 RECEPTOR ANTAGONIST—HYBRID FC FUSION PROTEIN

(75) Inventors: Young Gyu Cho, Seoul (KR); Hye Jeong Shin, Seoul (KR); Woon Young Lee, Seoul (KR); Woo Ick Jang, Seoul (KR)

(73) Assignees: Handok Pharmaceuticals, Inc., Seoul (KR), part interest; Genexine, Inc., Gyeonggi-do (KR), part interest ( * ) Notice: Subject to any disclaimer, the term of this patent is extended or adjusted under 35 U.S.C. 154(b) by 0 days.

(21) Appl. No.: 13/880,175

(22) PCT Filed: Oct. 19, 2011

(86) PCT No.: PCT/KR2011/007809
§ 371 (c)(1),
(2), (4) Date: Apr. 18, 2013

(87) PCT Pub. No.: WO2012/053828
PCT Pub. Date: Apr. 26, 2012

(65) Prior Publication Data
US 2013/0217864 A1    Aug. 22, 2013

(30) Foreign Application Priority Data

Oct. 20, 2010 (KR) .................. 10-2010-0102492
Oct. 19, 2011 (KR) .................. 10-2011-0107194

(51) Int. Cl.
| | | |
|---|---|---|
| A61K 38/20 | (2006.01) | |
| C07K 14/54 | (2006.01) | |
| C12N 15/62 | (2006.01) | |
| C07K 14/715 | (2006.01) | |
| C07K 16/18 | (2006.01) | |
| C07K 14/47 | (2006.01) | |

(52) U.S. Cl.
CPC ............. *C07K 16/18* (2013.01); *C07K 2319/30* (2013.01); *C07K 14/7155* (2013.01); *C07K 14/54* (2013.01); *C07K 14/4705* (2013.01)
USPC ......... 424/85.2; 530/351; 536/23.4; 536/23.5

(58) Field of Classification Search
CPC .. C07K 14/54; C07K 14/7155; C07K 14/705; C07K 2319/30
USPC ...................... 530/387.3; 536/23.4
See application file for complete search history.

(56) References Cited

U.S. PATENT DOCUMENTS

| | | | | |
|---|---|---|---|---|
| 5,116,964 | A | * | 5/1992 | Capon et al. .................. 536/23.5 |
| 6,294,170 | B1 | * | 9/2001 | Boone et al. ................ 424/134.1 |
| 6,337,072 | B1 | * | 1/2002 | Ford et al. .................. 424/198.1 |
| 7,148,321 | B2 | | 12/2006 | Gillies et al. |
| 8,066,994 | B2 | | 11/2011 | Gillies et al. |
| 8,110,665 | B2 | | 2/2012 | Kim et al. |
| 2008/0311111 | A1 | | 12/2008 | Drew et al. |
| 2010/0330108 | A1 | | 12/2010 | Song et al. |
| 2011/0091416 | A1 | | 4/2011 | Yang et al. |
| 2012/0114651 | A1 | | 5/2012 | De Wildt et al. |
| 2012/0276097 | A1 | | 11/2012 | Yang et al. |

FOREIGN PATENT DOCUMENTS

| | | | |
|---|---|---|---|
| EP | 1 366 067 B1 | | 9/2012 |
| KR | 10-2005-0047032 A | | 5/2005 |
| KR | 10-2007-0086896 A | | 8/2007 |
| KR | 10-2008-0077237 | | 8/2008 |
| WO | WO2004060911 | * | 7/2004 |
| WO | WO2007056812 | * | 5/2007 |

OTHER PUBLICATIONS

B Bresnihan "Effects of anakinra on clinical and radiological outcomes in rheumatoid arthritis" Ann Rheum Dis 2002;61(Suppl II):ii74-ii77.
E. William St. Clair "Tides of Inflammation: Impact of Biologics" The Journal of Rheumatology 2002, vol. 29, Supplement 65.
Zoey L. Fredericks et al. "Identification of potent human anti-IL-1RI antagonist antibodies" Protein Engineering, Design & Selection vol. 17 No. 1 pp. 95-06, 2004.
Mohammed F. Shamji "Development and Characterization of a Fusion Protein Between Thermally Responsive Elastin-like Polypeptide and Interleukin-1 Receptor Antagonist" 2007, American College of Rheumatology. Arthritis & Rheumatism vol. 56, No. 11, Nov. 2007, pp. 3650-3661.
Alain Beck and Janice M Reichert "Therapeutic Fc-fusion proteins and peptides as successful alternatives to antibodies" Landes Bioscience, mAbs 3:5, 415-416; Sep./Oct. 2011.
Bresnihan, "Effects of anakinra on clinical and radiological outcomes in rheumatoid arthritis", Ann Rheum Dis, vol. 61, Suppl II, pp. ii74-ii77, (2002).

* cited by examiner

*Primary Examiner* — Prema Mertz
(74) *Attorney, Agent, or Firm* — Vorys, Sater, Seymour and Pease LLP; Mihsun Koh

(57) ABSTRACT

The present disclosure provides a fusion protein comprising IL-1 receptor antagonist fused to a hybrid Fc. Particularly the present disclosure relates to a fusion protein comprising IL-1 receptor antagonist fused to a human immunoglobulin hybrid Fc fragment. In one embodiment, the hybrid Fc fragment comprises IgD and IgG4. Also provided is a pharmaceutical composition comprising the present fusion protein, which are useful for treating autoimmune disease including rheumatoid arthritis, inflammatory bowel disease (Crohn's disease, ulcerative colitis), psoriasis and diabetes and the like. The present fusion protein with excellent efficacy and reduced side effects is qualified for clinical development as therapeutic antibodies to treat autoimmune disease.

4 Claims, 22 Drawing Sheets

Primary Ab : anti-hIL-1RA

Lane 1 : Control Media

Lane 2 : Media from cells expressing hIL-1ra-hybrid Fc
fusion protein

Lane 3: Control, Lysate

Lane 4 : Lysates from cells expressing hIL-1ra-hybrid Fc
fusion protein

**Chromatogram of
Ab affinity column chromatography** a. Ab Affinity chromatography eluate electrophoresis
(12% SDS-PAGE, Reducing)
M: MW marker
L: Loading solution
F: Unbound solution
Elution: Eluted fraction b. Electrophoresis of eluate
(12% SDS-PAGE, non reducing)
M: MW marker
1: 5μg
2: 1μg

**Chromatogram of
Anion exchange resin column chromatography**

Electrophoresis of eluate
(12% SDS-PAGE, non reducing)
M: MW marker
L: Loading solution
Peak1: peak1 of the chromatogram of the eluate
Peak2: peak2 of the chromatogram of the eluate Isoelectric focusing electrophoresis
M: pI Marker
1, 2: Eluate of Ab affinity column
3: peak1 of Ion exchange resin column
4: peak2 of Ion exchange resin column
5: peak1 of hydroxyapatite column
6: peak2 of hydroxyapatite column SE-HPLC Chromatogram of purified IL-1 receptor blocker

SEQUENCE LISTING

```
<160> NUMBER OF SEQ ID NOS: 7

<210> SEQ ID NO 1
<211> LENGTH: 117
<212> TYPE: DNA
<213> ORGANISM: Artificial Sequence
<220> FEATURE:
<223> OTHER INFORMATION: DNA encoding partial hIL1 RA

<400> SEQUENCE: 1
gccaccatgg agatctgcag gggcctgagg tcccacctga tcaccctgct gctgttcctg      60
ttccactccg agaccatctg caggccctcc ggcaggaagt cctccaagat gcaggcc       117

<210> SEQ ID NO 2
<211> LENGTH: 138
<212> TYPE: DNA
<213> ORGANISM: Artificial Sequence
<220> FEATURE:
<223> OTHER INFORMATION: DNA encoding partial hIL1 RA
```

-continued

```
<400> SEQUENCE: 2
gatgggcacc acgtcgatct tctcctccag gttcacgttg ggccctgca ggtagccggc    60 caccagctgg ttgttcctca ggtagaaggt cttctggttc acgtcccaga tcctgaaggc   120
ctgcatcttg gaggactt                                                 138

<210> SEQ ID NO 3
<211> LENGTH: 147
<212> TYPE: DNA
<213> ORGANISM: Artificial Sequence
<220> FEATURE:
<223> OTHER INFORMATION: DNA encoding partial hIL1 RA

<400> SEQUENCE: 3
aagatcgacg tggtgcccat cgagccccac gccctgttcc tgggcatcca cggcggcaag    60
atgtgcctgt cctgcgtgaa gtccggcgac gagaccaggc tgcagctgga ggccgtgaac   120
atcaccgacc tgtccgagaa caggaag                                       147

<210> SEQ ID NO 4
<211> LENGTH: 138
<212> TYPE: DNA
<213> ORGANISM: Artificial Sequence
<220> FEATURE:
<223> OTHER INFORMATION: DNA encoding partial hIL1 RA

<400> SEQUENCE: 4
ggacacgggc tggtcggcct ccatggcggt gcacaggaac cagccggggc aggcggcgga    60
ctcgaaggag gtggtggggc cggagtcgga cctgatgaag gcgaacctct tgtcctgctt   120
cctattctcg gacaggtc                                                 138

<210> SEQ ID NO 5
<211> LENGTH: 105
<212> TYPE: DNA
<213> ORGANISM: Artificial Sequence
<220> FEATURE:
<223> OTHER INFORMATION: DNA encoding partial hIL1 RA

<400> SEQUENCE: 5
gccgaccagc ccgtgtccct gaccaacatg cccgacgagg gcgtgatggt gaccaagttc    60
tacttccagg aggacgaggg cggctcccgc aacaccggcc gcggc                   105

<210> SEQ ID NO 6
<211> LENGTH: 1278
<212> TYPE: DNA
<213> ORGANISM: Artificial Sequence
<220> FEATURE:
<223> OTHER INFORMATION: DNA encoding hIL1 RA-Hybrid Fc fusion protein

<400> SEQUENCE: 6
atggagatct gcaggggcct gaggtcccac tgatcaccc tgctgctgtt cctgttccac    60
tccgagacca tctgcaggcc ctccggcagg aagtcctcca agatgcaggc cttcaggatc   120
tgggacgtga accagaagac cttctacctg aggaacaacc agctggtggc cggctacctg   180
cagggcccca acgtgaacct ggaggagaag atcgacgtgg tgcccatcga gccccacgcc   240
ctgttcctgg gcatccacgg cggcaagatg tgcctgtcct gcgtgaagtc cggcgacgag   300
accaggctgc agctggaggc cgtgaacatc accgacctgt ccgagaatag gaagcaggac   360
aagaggttcg ccttcatcag gtccgactcc ggccccacca cctccttcga gtccgccgcc   420
```

```
tgccccggct ggttcctgtg caccgccatg gaggccgacc agcccgtgtc cctgaccaac      480
atgcccgacg agggcgtgat ggtgaccaag ttctacttcc aggaggacga gggcggctcc      540
cgcaacaccg ccgcggcgg cgaggagaag aagaaggaga aggagaagga ggagcaggag       600
gagcgcgaga ccaagacccc cgagtgcccc agccacaccc agcccctggg cgtgttcctg      660 ttcccccca agcccaagga caccctgatg atcagccgca ccccgaggt gacctgcgtg        720 gtcgtggatg tgagccagga agatcccgaa gtgcagttca actggtacgt ggatggcgtg     780
gaagtgcaca acgccaagac caagcccaga gaagagcagt tcaactccac ctacagagtg     840
gtgagcgtgc tgaccgtgct gcaccaggac tggctgaacg gcaaggagta caagtgcaag    900
gtgtccaaca aaggcctgcc cagctccatc gagaagacca tcagcaaagc caaaggccag    960
cccagagaac cccaggtgta caccctgcct cccagccagg aagagatgac caagaaccag     1020
gtgtccctga cctgcctggt gaaaggcttc taccccagcg acatcgccgt ggagtgggaa    1080
agcaacggcc agcccgagaa caattacaag acaaccccctc ccgtgctgga tagcgatggc  1140
agcttctttc tgtacagcag actgaccgtg gacaagagca gatggcagga aggcaacgtg   1200
ttcagctgca gcgtgatgca cgaagccctg cacaaccact acacccagaa gagcctgtcc    1260
ctgagcctgg gcaagtga                                                   1278

<210> SEQ ID NO 7
<211> LENGTH: 425
<212> TYPE: PRT
<213> ORGANISM: Artificial Sequence
<220> FEATURE:
<223> OTHER INFORMATION: Amino acid sequence of hIL1 RA-hybrid Fc fusion
      protein

<400> SEQUENCE: 7

Met Glu Ile Cys Arg Gly Leu Arg Ser His Leu Ile Thr Leu Leu Leu
  1               5                  10                  15

Phe Leu Phe His Ser Glu Thr Ile Cys Arg Pro Ser Gly Arg Lys Ser
                 20                  25                  30

Ser Lys Met Gln Ala Phe Arg Ile Trp Asp Val Asn Gln Lys Thr Phe
             35                  40                  45

Tyr Leu Arg Asn Asn Gln Leu Val Ala Gly Tyr Leu Gln Gly Pro Asn
         50                  55                  60

Val Asn Leu Glu Glu Lys Ile Asp Val Val Pro Ile Glu Pro His Ala
 65                  70                  75                  80

Leu Phe Leu Gly Ile His Gly Gly Lys Met Cys Leu Ser Cys Val Lys
                 85                  90                  95

Ser Gly Asp Glu Thr Arg Leu Gln Leu Glu Ala Val Asn Ile Thr Asp
                100                 105                 110

Leu Ser Glu Asn Arg Lys Gln Asp Lys Arg Phe Ala Phe Ile Arg Ser
            115                 120                 125

Asp Ser Gly Pro Thr Thr Ser Phe Glu Ser Ala Ala Cys Pro Gly Trp
        130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu Gly Gly Ser Arg Asn Thr Gly Arg Gly Glu Glu Lys Lys Lys
            180                 185                 190

Glu Lys Glu Lys Glu Glu Gln Glu Glu Arg Glu Thr Lys Thr Pro Glu
        195                 200                 205
```

```
Cys Pro Ser His Thr Gln Pro Leu Gly Val Phe Leu Phe Pro Pro Lys
    210                 215                 220

Pro Lys Asp Thr Leu Met Ile Ser Arg Thr Pro Glu Val Thr Cys Val
225                 230                 235                 240

Val Val Asp Val Ser Gln Glu Asp Pro Glu Val Gln Phe Asn Trp Tyr
                245                 250                 255

Val Asp Gly Val Glu Val His Asn Ala Lys Thr Lys Pro Arg Glu Glu
            260                 265                 270

Gln Phe Asn Ser Thr Tyr Arg Val Val Ser Val Leu Thr Val Leu His
        275                 280                 285

Gln Asp Trp Leu Asn Gly Lys Glu Tyr Lys Cys Lys Val Ser Asn Lys
    290                 295                 300

Gly Leu Pro Ser Ser Ile Glu Lys Thr Ile Ser Lys Ala Lys Gly Gln
305                 310                 315                 320

Pro Arg Glu Pro Gln Val Tyr Thr Leu Pro Pro Ser Gln Glu Glu Met
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
        355                 360                 365

Tyr Lys Thr Thr Pro Pro Val Leu Asp Ser Asp Gly Ser Phe Phe Leu
    370                 375                 380

Tyr Ser Arg Leu Thr Val Asp Lys Ser Arg Trp Gln Glu Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Leu Gly Lys
            420                 425
```

HUMAN INTERLEUKIN-1 RECEPTOR ANTAGONIST—HYBRID FC FUSION PROTEIN

The Sequence Listing submitted in text format (.txt) filed on Apr. 18, 2013, named "SequenceListing_Handok.txt", created on Apr. 17, 2013, 7.07 KB), is incorporated herein by reference.

CROSS-REFERENCE TO RELATED APPLICATIONS

The present application is a national stage application of International Patent Application No. PCT/KR2011/007809, filed Oct. 19, 2011, which claims the benefit of Korean Patent Application Nos. 10-2010-0102492 and 10-2011-0107194, filed Oct. 20, 2010, and Oct. 19, 2011, respectively, the disclosure of which are incorporated herein by reference in their entirety.

BACKGROUND OF INVENTION

1. Field of the Invention

The present disclosure relates to a fusion protein comprising human interleukin-1 receptor antagonist and hybrid Fc.

2. Description of the Related Art

Various monoclonal antibodies or fusion proteins, specifically binding to inflammatory cytokines, such as tumor necrosis factor-α (TNF-α), interleukin (IL)-1, IL-6 or receptor activator for nuclear factor κB ligand (RANKL), have been widely used to develop drugs for the inflammatory diseases. These drugs are targeting the diseases including inflammatory bowel disease (Crohn's disease, ulcerative colitis), rheumatoid arthritis and psoriasis and the like.

Among them, biological TNF-α inhibitors are leading the market at the present. However, its therapeutic applications have been limited by some problems, which include that all patients are not respond to TNF-alpha inhibitors and even if patients were respond to TNF-alpha inhibitors, the patients will not respond to TNF-alpha inhibitors after treatments of long period. Also since TNF-α plays an important role in a defense mechanism against bacterial and viral infections, the use of TNF-α blocker puts the patients at increased risk of serious infection, opportunistic infection and a recurrence of pneumonia. Therefore, there are needs for the development of new therapeutic agents for inflammatory autoimmune disease based on a novel mechanism of action that can replace the existing TNF-blockers.

Meanwhile, IL-1 receptor antagonist (IL-1Ra) is a natural IL-1 blocker found in the body and exerts their effects by competitively binding of IL-1 to its receptor (Fredericks, Zoey L et al., Protein Engineering, Design&Selection (2004) 17 (1): 95-106). In this regards, human recombinant IL-1 receptor antagonist (for example anakinra) has been developed and found to be effective in treating patients suffering from rheumatoid arthritis who do not respond to TNF-α inhibitors (Bresnihan, Ann. Rhem. Dis (2002); St. Clair, E. W. J. Rheumatol. (2002)). However, possibility of immunogenicity due to having extra methionine to produce in bacterial cells and short half-life around 2~3 hours requiring a daily injection remain to be the problems.

Also IL-1 receptor antagonist Fc fusion proteins had been expected to be effective in treating autoimmune disease by suppressing the activity of IL-1 which is the key factor in maintaining the inflammatory response. However, conventionally used for the construction of the fusion protein was the Fc derived from IgG1, and this caused antibody-dependent cell-mediated cytotoxicity (ADCC) and complement-dependent cytotoxicity (CDC), which led to the death of target cells. The resulting elimination of target cells may cause other safety concern of therapeutic agents.

SUMMARY OF THE INVENTION

The present inventors have found that the hybrid Fc fusion protein disclosed herein had have the increased half-life resulted from the FcRn binding, without compromising the activity of the therapeutic protein while the ADCC and CDC functions being eliminated.

Thus, the present disclosure is to provide a fusion protein of IL-1 receptor antagonist and hybrid Fc which is qualified for clinical development as therapeutic agents to treat inflammatory diseases.

In one aspect, the present disclosure is to provide a fusion protein comprising a human Interleukin 1-receptor antagonist fused to an immunoglobulin (Ig) hybrid Fc fragment derived from human.

In one embodiment, the Fc fragment includes fragments derived from IgD and IgG4.

Also the present disclosure is to provide a pharmaceutical composition comprising the fusion protein according to the present disclosure.

In one embodiment, the composition of the present disclosure is useful for treating inflammatory diseases, for example, such as rheumatoid arthritis, inflammatory bowel disease (for example Crohn's disease, ulcerative colitis), psoriasis and diabetes.

According to other aspect, the present disclosure is to provide a nucleic acid molecule encoding a fusion protein comprising Interleukin 1-receptor antagonist fused to an immunoglobulin (Ig) hybrid Fc fragment derived from human having a sequence comprising SEQ ID NO: 6.

According to other aspect, the present disclosure is to provide a fusion protein comprising Interleukin 1-receptor antagonist fused to an immunoglobulin (Ig) hybrid Fc fragment derived from human having a sequence comprising SEQ ID NO: 7.

The present IL-1 receptor antagonist-hybrid Fc fusion proteins have the advantages compared to the conventional recombinant human IL-1 receptor antagonist and IL-1 receptor antagonist type/Fc fusion proteins, which include an increased stability and bioavailability in vivo, less toxicity to cells and low immunogenicity.

The foregoing summary is illustrative only and is not intended to be in any way limiting. Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 8a is a chromatogram from anion exchange column chromatography analysis and FIG. 8b is a PAGE result showing quantitative and qualitative analysis of the peaks identified in FIG. 8a.

FIG. 9a is a chromatogram result from hydroxy apatite column chromatography analysis and FIG. 9b is a PAGE result showing quantitative and qualitative analysis of the peaks identified in FIG. 9a.

DETAILED DESCRIPTION OF THE EMBODIMENTS

Figure 1:
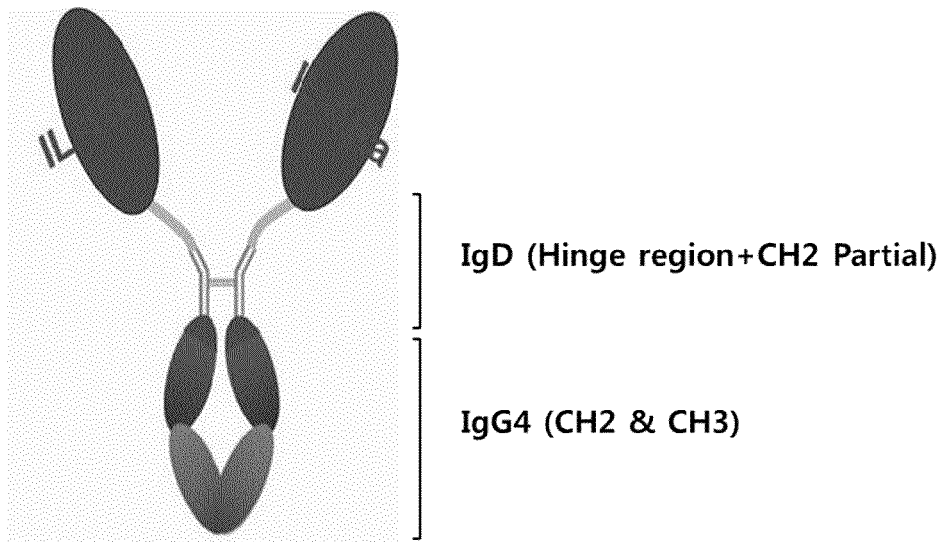
FIG. 1 is an illustrative schematic diagram of a human IL-1 receptor antagonist (IL-1Ra) fused to the Fc portion of an immunoglobulin molecule derived from human (hybrid Fc).

In one aspect, the present disclosure relates to a fusion protein comprising a human IL-1 receptor antagonist (IL-1Ra) and a human immunoglobulin hybrid Fc fragment (hybrid Fc) (Refer to FIG. 1). In one embodiment, the IL-1Ra of the present disclosure is a whole protein, which is linked to hybrid Fc through a linker. In one embodiment, the linker which may be used for the present disclosure includes a synthetic linker, which for example consists of Glycine and Serine amino acids. In one embodiment, the linker is composed of GGS. The hybrid Fc includes from N-terminal to C-terminal, a hinge region, CH2 domain and CH3 domain. In one embodiment, the hinge region includes a region from IgD, CH2 domain includes regions derived at least from human IgD and IgG4, and CH3 domain include a region derived at least from human IgG4 CH3 domain.

Interleukin-1, together with TNF-alpha, acts as a crucial inflammatory mediator in amplifying an inflammatory response in the development of autoimmune inflammatory disease. Also IL-1 recruits neutrophils to inflammatory sites and activates macrophages, and activates the growth and differentiation of T and B cells. IL-1 receptor antagonist (IL-1Ra) is a protein naturally found in body that suppresses the IL-1 activity via competitively binding of IL-1 to its receptor.

Conventionally, Fc derived from IgG1 has been used for the generation of fusion protein with IL-1Ra. However, as described hereinbefore, it caused ADCC (antibody dependent cell-mediated cytotoxicity) and CDC (Complement-dependent cytotoxicity) which may cause safety concern.

The fusion protein of the present disclosure contains a hybrid Fc which comprises Fc region selected from IgG4 and IgD. The characteristics of the subclasses of IgG and IgD are described in Table 1 below.

|  | IgG1 | IgG2 | IgG3 | IgG4 | IgD | Potential Effect |
|---|---|---|---|---|---|---|
| Flexibility of hinge | +++ | ++ | ++++ | ++ | ++++ | Increase efficacy |
| Binding ability of macrophages to Fc gamma receptor | ++++ | +/− | ++++ | ++ | − | Reduced side effects |
| Activation of complement system | ++ | + | +++ | − | − | Reduced side effects |
| Binding activity to FcRn | ++++ | ++++ | − | ++++ | − | Increased half life |
| In vivo half life (Days) | 21 | 21 | 7 | 21 | 3 | — |

The hybrid Fc of the present disclosure has an favorable conformation resulted from the flexibility of the hinge region derived from IgD and also a reduced side effect due to the lack of Fc gamma Receptor binding region, which acts as a receptor for Fc present in neutrophils. IgG4 does not have an effector function such as CDC and thus is able to reduce the unwanted immune responses and also shows an increased half-life and stability resulted from the excellent ability to bind FcRn which is related to recycling of proteins in cells. With regard to half-lives in cells, IgG1, IgG2 and IgG4 have a half-life of 21 days compared to other immunoglobulines which have a relatively short half-life of less than a week. The fusion protein of the present disclosure comprising Fc selected from IgD and IgG4 shows a favorable efficacy in activity and an increased half-life while having a reduced side effect. Also the IL-1 receptor antagonist-hybrid Fc fusion protein, which was produced in mammalian cells such as CHO cells, has a reduced immunogenicity due to glycosylation and absence of abnormal amino acids in contrast to anakinra which are normally produced in *Escherichia coli*.

The present disclosure is further explained in more detail with reference to the following examples. These examples, however, should not be interpreted as limiting the scope of the present invention in any manner.

EXAMPLES

Example 1

Construction of a Plasmid Encoding IL1 Ra-hyFc Fusion Protein

For cloning, DNA fragment encoding Human IL-1Ra was codon optimized and synthesized in several fragments as indicated below and combined into a full length hIL-1Ra DNA by sewing PCR. A DNA encoding IL-1 receptor antagonist-hybrid Fc fusion protein (IL-1Ra-hyFc) was generated by PCR-combining DNA encoding hybrid Fc (hyFc) was provided by Genexine (Korea) and DNA fragment with hIL-1Ra prepared above.

For the construction of plasmid, pAD15 vector, containing expression cassette for beta-lactamase and dihydrofolate reductase (DHFR), was used. Both the vector and the DNA fragment encoding IL1-Ra-hyFc as prepared above were digested with EcoRI and XbaI and purified, which were then ligated to obtain a final construct, IL-1Ra-hyFc/pAD15. The ligated product was then transformed into DH5 alpha competent cells and the transformed cells were selected on a plate containing ampicillin. The selected colonies were then used for the DNA sequencing analysis for confirmation.

[Sequences of Regions of IL-1 Ra Genes Synthesized for the Construction of Plasmid]

```
F-1:
gcc acc atg gag atc tgc agg ggc ctg agg tcc cac ctg atc acc ctg ctg ttc ctg ttc cac tcc gag acc atc tgc agg ccc tcc ggc agg aag tcc tcc aag atg cag gcc R-2:
gat ggg cac cac gtc gat ctt ctc ctc cag gtt cac gtt ggg gcc ctg cag gta gcc ggc cac cag ctg gtt gtt cct cag gta gaa ggt ctt ctg gtt cac gtc cca gat cct gaa ggc ctg cat ctt gga gga ctt F-3:
aag atc gac gtg gtg ccc atc gag ccc cac gcc ctg ttc ctg ggc atc cac ggc ggc aag atg tgc ctg tcc tgc gtg aag tcc ggc gac gag acc agg ctg cag ctg gag gcc gtg aac atc acc gac ctg tcc gag aac agg aag R-4:
gga cac ggg ctg gtc ggc ctc cat ggc ggt gca cag gaa cca gcc ggg gca ggc ggc gga ctc gaa gga ggt ggt ggg gcc gga gtc gga cct gat gaa ggc gaa cct ctt gtc ctg ctt cct att ctc gga cag gtc F-5:
gcc gac cag ccc gtg tcc ctg acc aac atg ccc gac gag ggc gtg atg gtg acc aag ttc tac ttc cag gag gac gag ggc ggc tcc cgc aac acc ggc cgc ggc
```

The Sequences F-1 to F-5 encoding part of hIL-1Ra indicated as above are disclosed as SEQ ID NOs: 1 to 5, respectively. The entire sequences of final IL-1 RA synthesized are indicated as below, which is disclosed as SEQ ID NO: 7.

```
atg gag atc tgc agg ggc ctg agg tcc cac ctg atc acc ctg ctg ttc ctg ttc cac tcc gag acc atc tgc agg ccc tcc ggc agg aag tcc tcc aag atg cag gcc ttc agg atc tgg gac gtg aac cag aag acc ttc tac ctg agg aac aac cag ctg gtg gcc ggc tac ctg cag ggc ccc aac gtg aac ctg gag gag aag atc gac gtg gtg ccc atc gag ccc cac gcc ctg ttc ctg ggc atc cac ggc ggc aag atg tgc ctg tcc tgc gtg aag tcc ggc gac gag acc agg ctg cag ctg gag gcc gtg aac atc acc
```

-continued

```
gac ctg tcc gag aat agg aag cag gac aag agg ttc gcc ttc atc agg tcc gac tcc ggc ccc acc acc tcc ttc gag tcc gcc gcc tgc ccc ggc tgg ttc ctg tgc acc gcc atg gag gcc gac cag ccc gtg tcc ctg acc aac atg ccc gac gag ggc gtg atg gtg acc aag ttc tac ttc cag gag gac gag ggc ggc tcc cgc aac acc ggc cgc ggc ggc gag gag aag aag aag gag aag gag aag gag gag cag gag gag cgc gag acc aag ace ccc gag tgc ccc agc cac ace cag ccc ctg ggc gtg ttc ctg ttc ccc ccc aag ccc aag gac acc ctg atg atc agc cgc acc ccc gag gtg acc tgc gtg gtc gtg gat gtg agc cag gaa gat ccc gaa gtg cag ttc aac tgg tac gtg gat ggc gtg gaa gtg cac aac gcc aag acc aag ccc aga gaa gag cag ttc aac tcc acc tac aga gtg gtg agc gtg ctg acc gtg ctg cac cag gac tgg ctg aac ggc aag gag tac aag tgc aag gtg tcc aac aaa ggc ctg ccc agc tcc atc gag aag acc atc agc aaa gcc aaa ggc cag ccc aga gaa ccc cag gtg tac acc ctg cct ccc agc cag gaa gag atg acc aag aac cag gtg tcc ctg ace tgc ctg gtg aaa ggc ttc tac ccc agc gac atc gcc gtg gag
```

Figure 2:
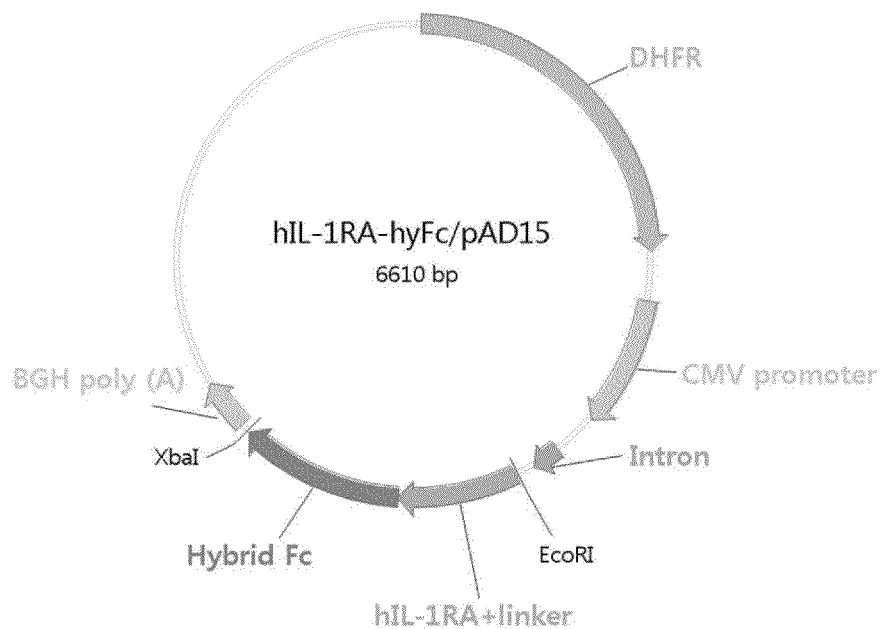
FIG. 2 is an illustrative recombinant plasmid map according to one embodiment of the present disclosure where DNA encoding IL-1 receptor antagonist-hybrid Fc fusion protein was inserted.

The amino acid sequence of the present IL-1 receptor antagonist-hybrid Fc fusion protein is disclosed as SEQ ID NO:7. FIG. 2 shows a map of the plasmid IL-1Ra-hyFc/pAD15 constructed herein having 6610 bps in size.

Example 2

Establishment of Cell Lines Expressing the Present Fusion Protein

(1) Transfection

The plasmid constructed in Example 1 was transfected into a mammalian cell line CHO DG44 to confirm the expression of fusion protein.

Specifically $4 \times 10^5$ CHO DG44 cells were seeded on to a 6 well culture plate. One day after, culture media was changed with fresh media (Minimum Essential Medium Alpha). The DNA and liposomal mixture, PEI (Polyethylenimine) and expression plasmid, IL-1Ra-hyFc/pAD15, were then added into the culture media of CHO DG44 cells as prepared above. The culture media were replaced with fresh one, after 12 hours.

(2) Selection of Cells Expressing the Protein

The CHO DG44 cells expressing IL1Ra-hyFc fusion protein were selected based on the Hypoxanthine (HT) system. CHO DG44 cells transfected with a vector, IL1Ra-hyFc/pAD15, were screened with media lacking HT at 24 hours after the transfection. The media were replaced with fresh one every 3-4 days until colonies were formed, the colonies were picked and transferred into new plates.

Figure 3:
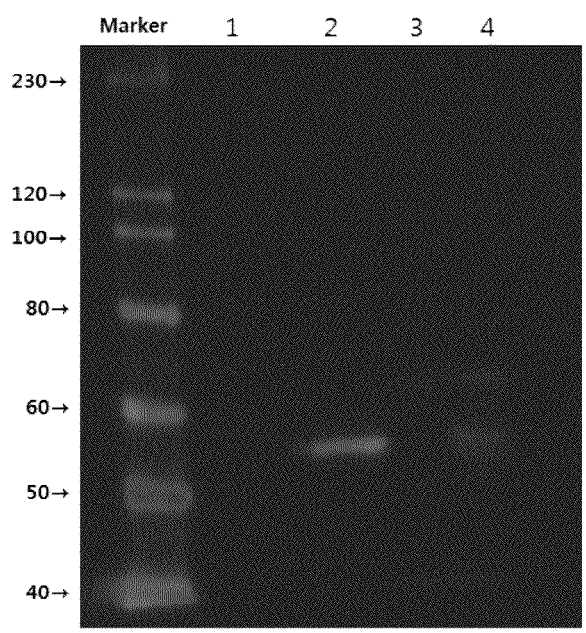
FIG. 3 is a immunobloting result showing the expression of IL-1 receptor antagonist-hybrid Fc fusion protein according to one embodiment of the present disclosure in CHO DG44 cells.

FIG. 3 is a result of western blot analysis with anti-IL1Ra antibody to confirm the expression of IL1Ra-hyFc fusion protein in the selected cells. FIG. 3 shows that the cells selected as above successfully expressed and secreted the protein into media as shown in lane 2, and 4. However, the control cells did not produce the protein (lane 1, and 3).

(3) Determination of the Productivity of the Cells

Figure 4:
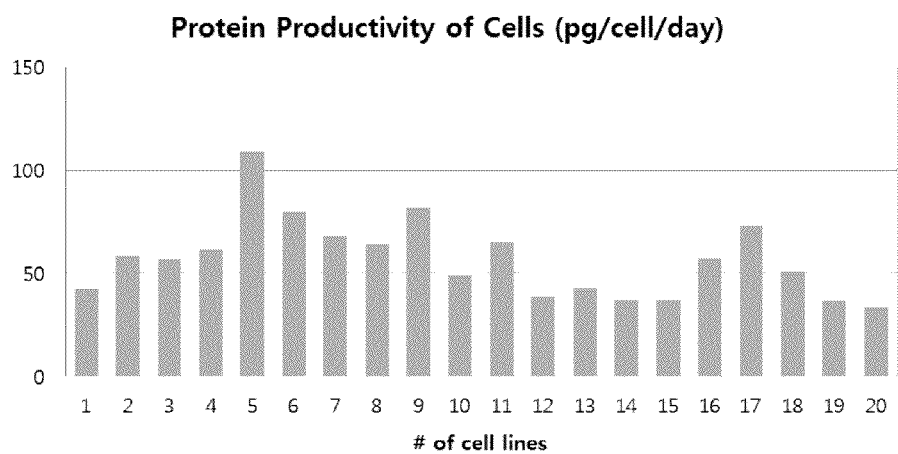
FIG. 4 is a result showing the productivity of the cells selected for the production of IL-1 receptor antagonist-hybrid Fc fusion protein according to one embodiment of the present disclosure.

The clones expressing IL1Ra-hyFc fusion protein were incubated in fresh media for 24 hours, the media of which were then collected and the number of cells was counted. The unit cell production of protein was determined by ELISA quantitation kit (Bethyl lab., Inc., E80-104). The unit cell productivity of protein (pg/cell/day) by was determined dividing the amount of proteins calculated from ELISA quantitation by the total number of cells. As indicated in FIG. 4, the representative cell lines selected based on the HT system as above, expressed the fusion protein with varying productivity (pg/cell/day).

Example 3

Confirmation of Protein Expression by Western Blotting

Figure 5:
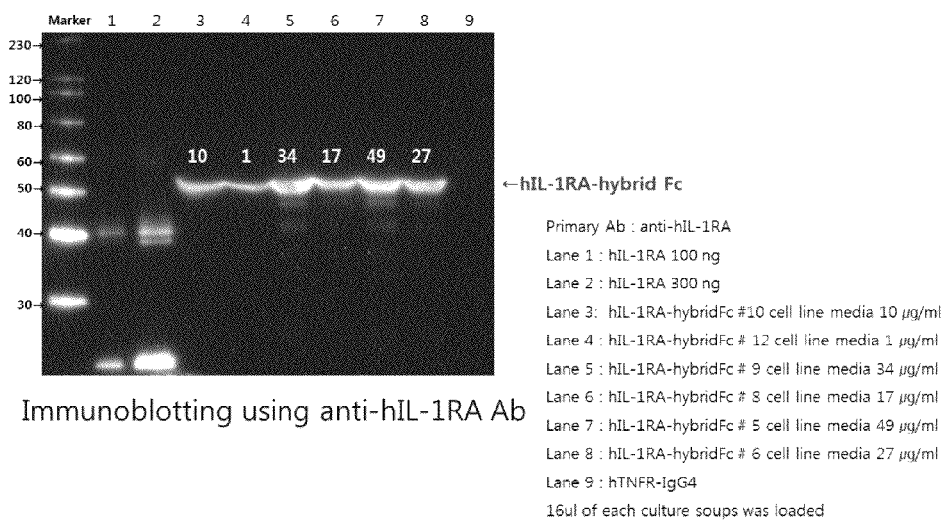
FIG. 5 is a immunoblotting result showing quantitative and qualitative analysis of IL-1 receptor antagonist-hybrid Fc fusion proteins produced from the cells selected.

The proteins expressed were confirmed by western blot with anti-IL1ra antibody (abcam, USA). The proteins of culture supernatant of the selected clones were separated on 12% SDS-PAGE, then transferred on to the nitrocellulose membrane. The Il1ra-hyFc and Il1ra protein was detected with anti-IL1ra antibody. Results are shown in FIG. 5.

The fusion protein, expressed in each of the cell lines, has a molecular weight of about 55 kDa. When it was compared to hIL-1RA, its molecular weight has increased 30 kDa due to the fusion with the hybrid Fc.

Example 4

Purification and Concentration of Protein

(1) Purification Using Antibody Affinity Chromatography

The supernatant containing IL1Ra-hyFc fusion protein obtained from suspension cell culture was filtered through a cellulose filter (pore size 0.2 μm) to remove impurities and the filtrated protein were stored at 4° C. or on ice. IL1Ra-hyFc protein was purified by affinity chromatography. Mobile phase was prepared by loading the Mabselect Sure(GE) into column, a type of antibody affinity column resin which is labeled with Protein A. First of all, buffer A which is used for equilibrating column and composed of 50 mM $NaH_2PO_4$ (pH8.0) and 0.1M NaCl was prepared. Then buffer B for elution of bound proteins under acidic condition was composed of 50 mM $NaH_2PO_4$ (pH8.0) and 0.1M NaCl (pH3.0). Further, buffer C for elution of proteins that remained after the elution with buffer B was composed of 0.5M arginine (pH3.0) and 0.1M NaCl. The last buffer D for CIP was composed of 0.5N NaOH. Each line of the chromatography system (AKTA Purifier, GE healthcare) was washed with each of buffer A~D as prepared above and then the antibody affinity chromatography column which was loaded with 20 ml of Mabselect Sure was equipped with the chromatography system, The column was equilibrated with 10 CV (column volume). After confirming of the equilibration, the supernatant contained IL1Ra-hyFc fusion protein was loaded onto the column for purification. The bound proteins were eluted using buffer B and collected as an aliquot of 3 ml. The purified proteins were electrophoresed on a 12% SDS-PAGE (Sodium Dodecyl-Sulfate Poly Acrylamide Gel Electrophoresis under reducing condition and confirmed the bands corresponding to 50 kDa. And then the fusion protein was quantitated using Bradford protein assay (FIGS. 6 and 7).

Figure 6:
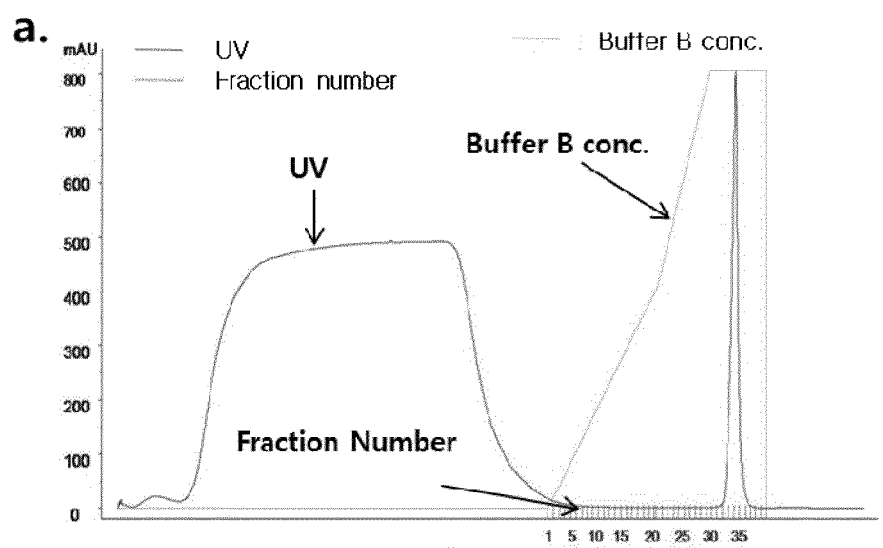
FIG. 6 is a chromatogram result from antibody affinity column chromatography of IL-1 receptor antagonist-hybrid Fc fusion proteins according to one embodiment of the present disclosure.
Figure 7:
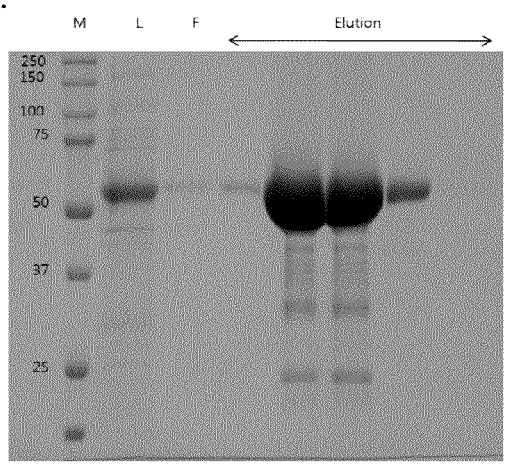
FIG. 7 is a PAGE result showing quantitative and qualitative analysis of the peaks identified in FIG. 6. The PAGEs of FIGS. 7a and 7b were performed on a 12% SDS-PAGE under a reducing condition and a non-reducing condition, respectively.
Figure 7:
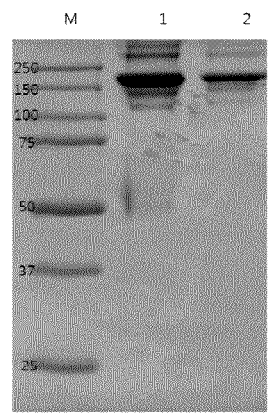

FIG. 6 indicates the chromatogram of the antibody affinity column chromatography as above, and shows that the eluted fusion proteins using buffer B are present in peaks numbered from 30 to 40. As shown in FIG. 7a, the purified protein sample was analyzed as quantitative and qualitative using 12% SDS-PAGE. The results show that the purified fusion protein which exists in 50 KDa position was obtained almost from eluted peak fraction. The purity was confirmed to be at least 95%. FIG. 7b shows that band position of the fusion protein was confirmed in 150 KDa by using 12% SDS-PAGE under non reducing condition, due to the dimer formation of the fusion protein through disulfide bonds.

(2) Purification Using Anion Exchange Resin Chromatography

Figure 8:
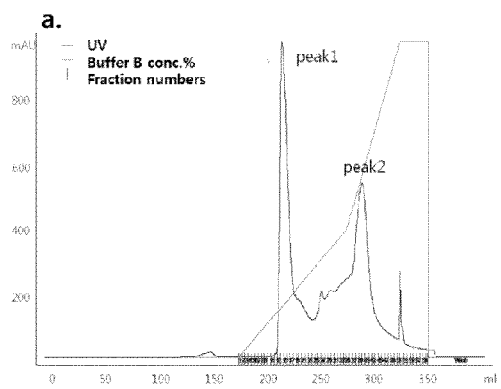
Figure 8:
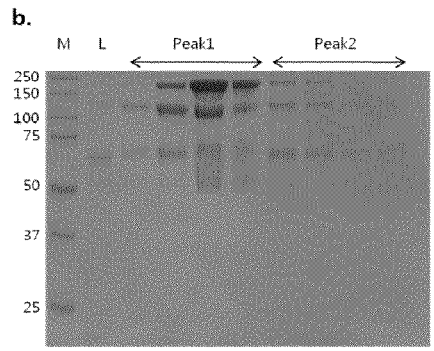

Protein solution obtained from the antibody affinity column chromatography was prepared in 50 mM Tris-HCl (pH8.0) using 1M Tirs-HCl (pH8.0) and incubated at RT for 30 min. Then two volumes of 50 mM Tris-HCl (pH8.0) solution were added to the protein preparation to reduce the NaCl concentration for loading onto the anion exchange chromatography column. Equilibration buffer A of 50 mM Tris-HCl (pH8.0) and elution buffer B 50 mM Tris-HCl (pH8.0) of 1M NaCl was added to fill the Anion exchange resin (AKTA Purifier, Q HP, GE) and the protein prepared as above was loaded on the anion exchange column. Dimers and multimers of IL-1 receptor antagonist-hybrid Fc fusion protein were eluted with buffer B using a NaCl concentration gradient. The dimers were present in the peaks eluting around 300 mM of NaCl (FIG. 8a, peak 1) and heterogeneous mixture of dimers and multimers are present in the peaks eluting NaCl concentration above 500 mM (FIG. 8a, peak 2). Proteins from peaks 1 and 2 show SDS-PAGE analysis under non-reducing condition as shown in FIG. 8.

(3) Purification Using Hydroxyapatite Column Chromatography

Figure 9:
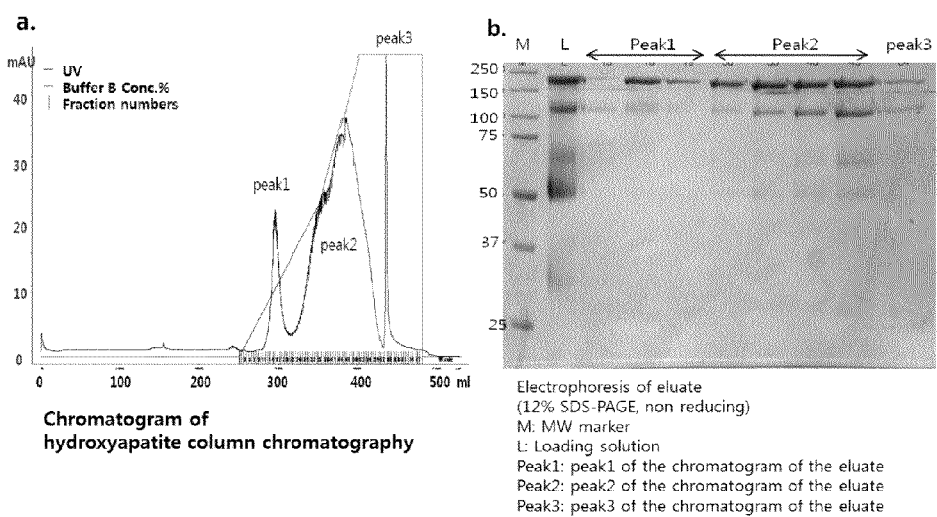

For mobile phase of hydroxyapatite column (CHTTM Ceramic Hydroxyapatite, BIO-RAD), 10 mM $Na_2HPO_4$ (pH6.5) was used as column equilibration buffer, for elution, 10 mM $Na_2HPO_4$ (pH6.5), 2M NaCl and 500 mM $Na_2HPO_4$ (pH6.5) were used. Dimer fraction from the anion exchange column was diluted with the equilibration buffer in 5 times volume before loaded onto the hydroxyapatite column. A gradient of increasing NaCl concentration and $Na_2HPO_4$ concentration was applied to the column to obtain IL-1 receptor antagonist hybrid Fc fusion proteins in a highly purified form. Peaks were eluted at each of the NaCl concentrations below 1M and 2M, obtain only the peak below 1M NaCl was taken for further analysis where the majority of proteins are present in dimer (FIG. 9a). FIG. 9b shows the result of SDS-PAGE analysis of the peaks from the hydroxyapatite column purification under non reducing condition to confirm the proteins contained in each peaks. The purified proteins were quantified using Bradford method and concentrated using ultrafiltration.

Example 5

Characterization of hIL1 RA-hFC Fusion Protein

Figure 10:
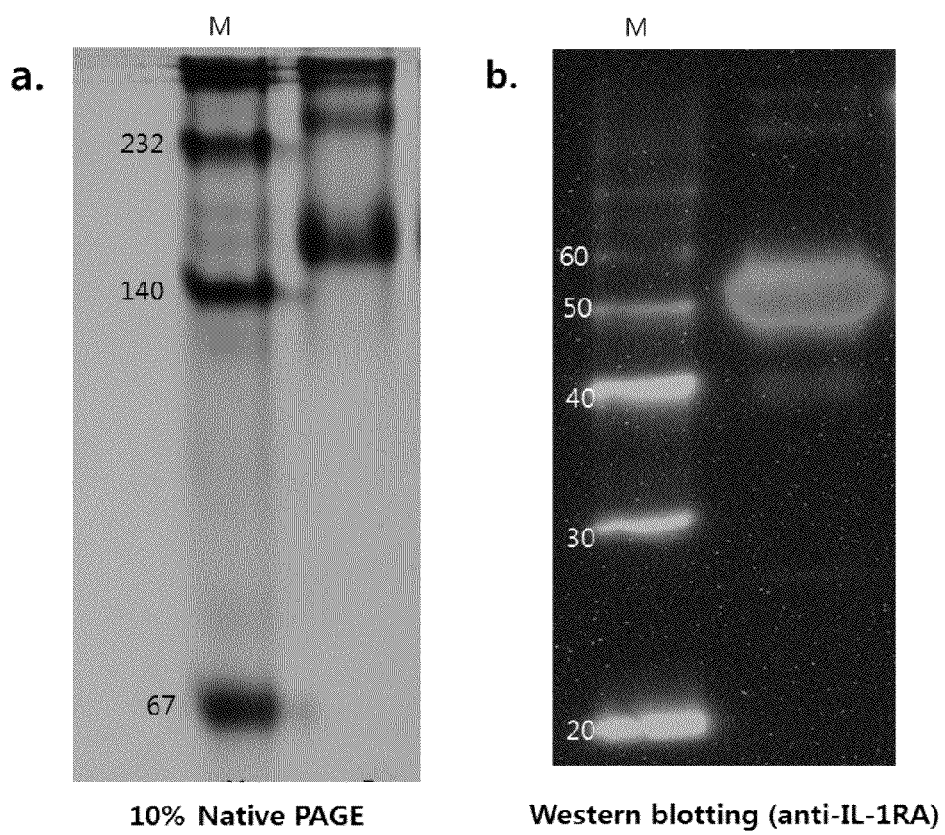
FIG. 10a is a non-denaturing electrophoresis result and FIG. 10b is an immunoblot result from denaturing PAGE, performed on IL-1 receptor antagonist-hybrid Fc fusion proteins according to one embodiment of the present disclosure.
Figure 11:
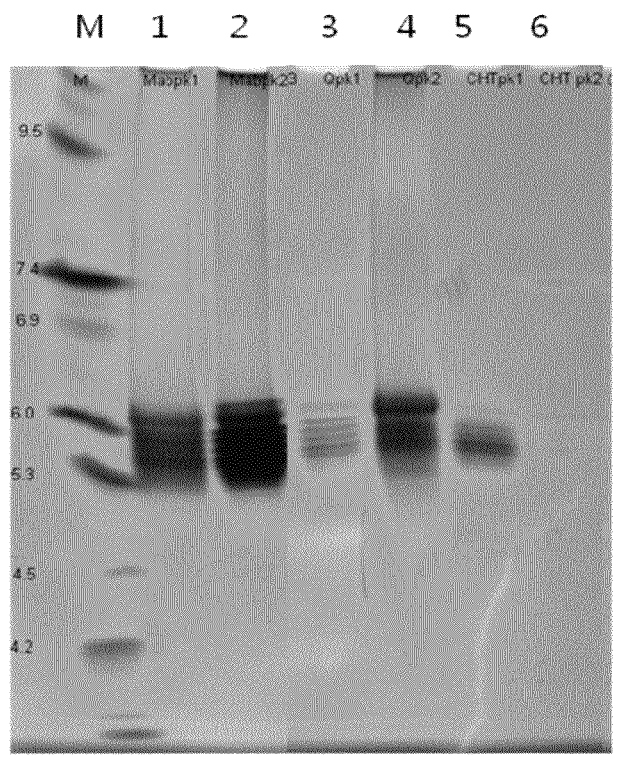
FIG. 11 is an isoelectric electrophoresis result performed on IL-1 receptor antagonist-hybrid Fc fusion proteins according to one embodiment of the present disclosure.
Figure 12:
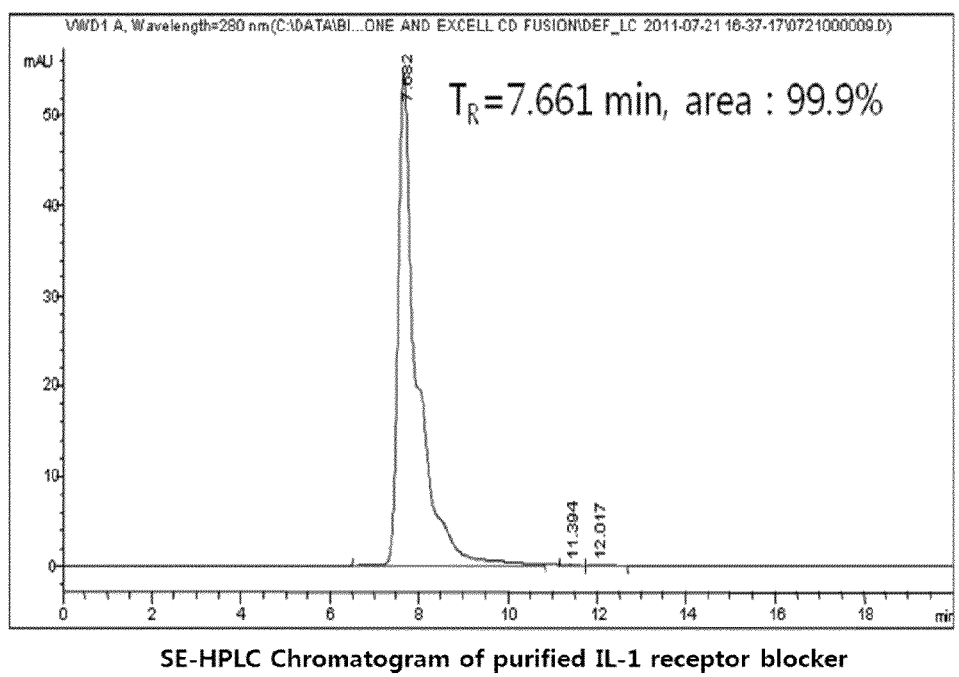
FIG. 12 is a chromatogram result of SE-HPLC chromatography performed on a purified IL-1 receptor antagonist-hybrid Fc fusion protein according to one embodiment of the present disclosure.

Native gel electrophoresis, western blot, isoelectric focusing, and size exclusion HPLC (SE-HPLC) were performed to characterize the protein purified as above. Results are shown in FIGS. 10 to 12. As shown in FIG. 10a, in the non-denaturing electrophoresis using 10% polyacrylamide gel, IL1Ra-hyFc fusion proteins was confirmed to be present as dimer by the 150 kDa band position judged by the molecular weight marker (GE Healthcare, Amersham™ HMW Calibration Kit For Native Electrophoresis). In addition, as shown in FIG. 10b, IL-1Ra-hyFc fusion proteins were confirmed in the western blot analysis using anti-hIL-1RA antibody.

Theoretical value of isoelectric point of IL-1Ra-hyFc fusion protein is 6.01. In the experiment, the value was in the range from pI 5.3 to 6.0 at the beginning of the purification and became close to the one value as the purification progressed. This indicates the increasing homogeneity in the form.

Twenty μl of sample was loaded onto a SEC HPLC column (G3000SWXL, 5 micron, 7.8*300, TSK, Agilent) in the mobile phase of 50 mM Sodium phosphate (pH7.5) and 50 mM NaCl. Then, a peak was eluted at retention time of 7.6 (purity 99.9%). The peak is indicated the presence of highly purified proteins.

Example 6

Determination and Comparison of Binding Affinity

To compare the binding affinity of the IL1Ra-hyFc fusion protein and hIL-1RA fused with Fc from IgG1 to hIL-1 RI, surface plasmon resonance (SPR) value was measured using Biacore (GE Healthcare).

CM5 chip set up to Biacore and then PBS (Phosphate buffered saline, PBS) was flowed into the CM5 chip. After the confirming that the baseline of the graph remained constant, 1-ethyl-3-dimethylaminopropyl carbodiimide (EDC)/N-hydroxy succinimide (NHS) was add to the chip to activate the amine group. Next, the IL1Ra-hyFc fusion protein or hIL-1RA fused with Fc from IgG1 was introduced to the chip to fix the proteins via covalent linkage with the activated amine group followed by additional fixation using ethanol amine. Then hIL-1RI protein was introduced into the chip to measure the resonance unit (RU), which represent the binding affinity. From this results dissociation constant (Kd) was calculated.

Figure 13:
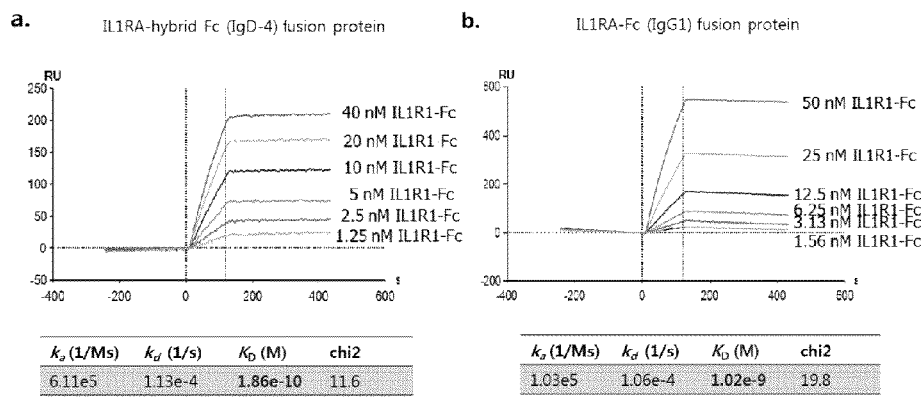
FIG. 13 is an affinity analysis result in which a purified IL-1 receptor antagonist-hybrid Fc fusion protein according to one embodiment of the present disclosure or IL-1 receptor antagonist fused to IgG1 Fc as a control binds to an IL-1 receptor.

As indicated in FIG. 13, the IL1Ra-hyFc fusion protein has a dissociation constant of 186 pM in comparison to the control which has a dissociation constant of 1.02 nM. The results indicate that the present protein has better affinity than that of the control.

Example 7

Anti-Inflammatory Effect in Human Cells

To test the effect of the IL1Ra-hyFc fusion protein on suppressing an immune response, the suppression of T cell proliferation and the secretion of inflammatory cytokines were measured. For the former, peripheral blood mononuclear cells were isolated from blood. After the PBMC was diluted with RPMI-1640 medium as the concentration of $1\times10^5$ cells/ml, the cells were stimulated with 100 ng/ml of LPS (lipopolysaccharide) or 1 μg/ml of anti-CD3 antibody for 3 days in the absence or in the presence of various concentrations of the IL1Ra-hyFc fusion proteins. During the last 18 hours of the stimulation period at day 3, the cells were incubated in the presence of 1 mCi [$^3$H]thymidine (NEN, Boston, Ma., USA). After the cells were then transferred onto a nitrocellulose membrane followed by washing, the amount of radioactivity remained on the membrane was measured.

To measure the amount of inflammatory cytokines secreted, PBMC were isolated from blood. After the PBMC was diluted with RPMI-1640 medium as the concentration of $1\times10^6$ cells/ml, then the PBMC was stimulated with 100 ng/ml of LPS for 48 hours in the absence or presence of the present fusion protein in various concentrations. After 48 hours, the media was collected and the levels of interleukin-17, TNF-alpha (Tumor necrosis factor-alpha), RANKL (Receptor Activator of Nuclear factor k-B ligand) and VEGF (Vascular Endothelial Growth Factor) were measured using ELISA.

Figure 14:
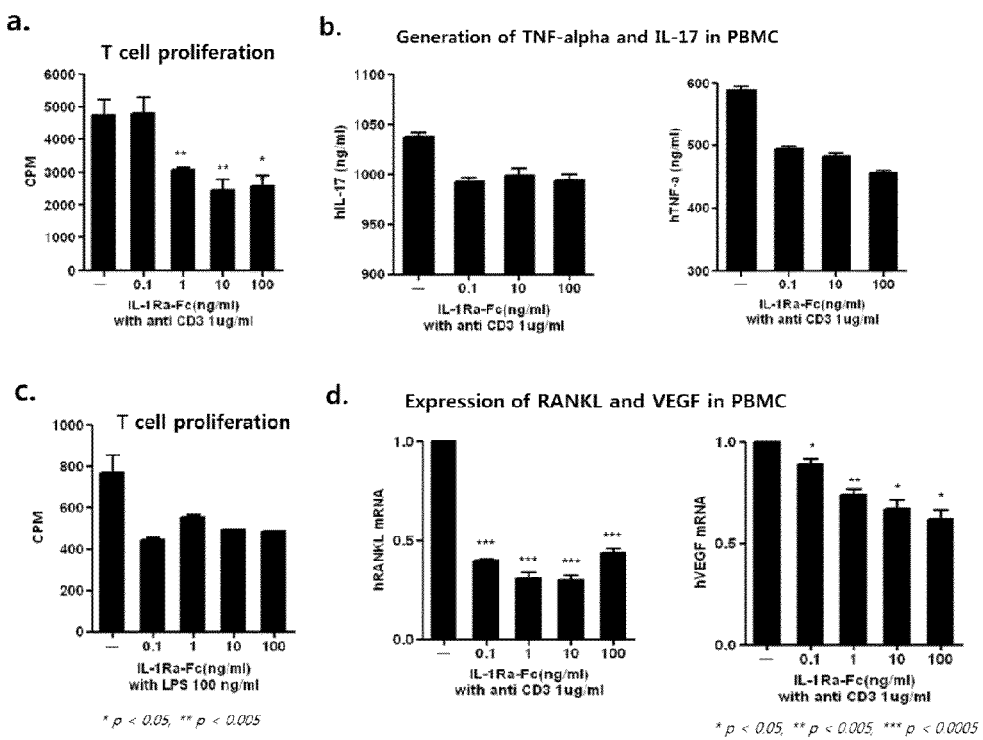
FIG. 14 is a result showing that IL-1 receptor antagonist-hybrid Fc fusion protein according to one embodiment of the present disclosure inhibits the T cell proliferation or production of inflammatory cytokines in peripheral blood monocytes.

FIG. 14 presents that the IL1Ra-hyFc fusion protein suppress the immune response in human T cell or PBMC. As shown in FIG. 14, when the fusion protein was treated, we confirmed that T cell proliferation was effectively suppressed in the presence of the fusion protein. Also the fusion protein was effectively suppressed the inflammatory cytokines and cytokines which is involved in osteoclasia.

Example 8

Measurement of Pharmacokinetics

Healthy female Balb/c mice in 6 weeks of age were treated with Anakinra, a commercially available IL-1 receptor antagonist, or with the present fusion protein each at 5 mg/kg of dosage via intraperitoneal. At 0, 0.05, 0.5, 2, 4, 6, 8, 24, 30, and 48 hours after the injection, blood samples were collected from each of the mice and the levels of anakinra or the fusion protein were measured using ELISA. 100 µl of affinity purified Human IgG capture antibody (Bethyl Laboratories, Inc., A80-104A-6) diluted with coating buffer was added to each well of plate and the plate was incubated at RT for 1 hour. Then the plate was washed 5 times with TBST (Tris-Buffered Saline Tween-20) and 200 µl of blocking buffer containing 1% BSA (Bovine serum albumin) was added to each well. The plate was incubated for 30 min at RT and then washed 5 times with TBST. 100 µl of standard solution in two fold serial dilution from 500 pg/ml to 0 pg/ml or the blood samples appropriately diluted were added to each well and incubated 1 hour at RT. After the incubation, the plate was washed 5 times with TBST and 400 ng/ml of biotin conjugated anti-hIL-1RA polyclonal detection antibody was added to each well and the plate was incubated for 1 hour at 20-25° C. The plate was then washed 5 times with TBST and incubated with 100 µl of Streptavidin HRP conjugated antibody diluted at a ratio of 1:50000 for 1 hour at 20-25° C. Then the plate was washed 5 times with TBST and 100 µl of TMB substrate was added to each well and the plate was incubated in the dark for 15 min at RT. The reaction was terminated by adding 100 µl of stop buffer and the absorbance was measured in a plate reader at 450 nm. The concentration of the protein was calculated as ng/ml by multiplying the value obtained from ELISA by dilution factor.

Figure 15:
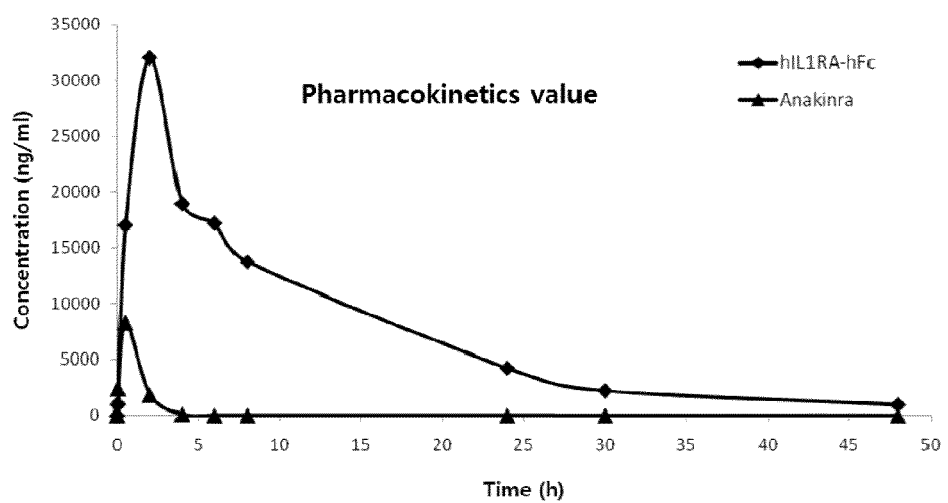
FIG. 15 is a rat pharmacokinetic result performed on IL-1 receptor antagonist-hybrid Fc fusion protein according to one embodiment of the present disclosure and Anakinra, an IL-1 receptor antagonist, as a control which is available in Europe.

FIG. 15 presents the pharmacokinetic data using the fusion protein or anakinra which is commercially available in Europe. As shown in FIG. 15, the fusion protein remains longer period of time in the blood than that of anakinra.

Example 9

Luciferase Assay (1) Blocking of the hIL-1beta Signal Transduction Pathway by the Present Fusion Protein Luciferase assay was performed to measure the effect of the fusion protein on blocking the hIL-1beta signal transduction pathway.

Human IL-1beta activates NFkB by binding to hIL-1 receptor 1 through signal transduction. To confirm that, cells expressing hIL-1 receptor 1 were transfected with a luciferase vector having a NFkB binding site. Then the cells treated with hIL-1beta followed by measuring the luciferase expression as the results of NFkB activation. Here, the addition of IL-1 RA blocks the luciferase expression by competitive binding to hIL-1 receptor 1 with hIL-1beta. Thus the function of the fusion protein in cells was tested on the basis of this scheme.

HeLa cells ($2\times10^4$) were seeded in each well of 48 well plate at 24 hours prior to transfection. Next day, the cells were co-transfected with a firefly luciferase plasmid having a NFkB binding site and a renilla luciferase plasmid having CMV promoter which is used to normalize the result. Three hours after the transfection, cells were replaced with fresh media and stabilized for 24 hours. The varying concentrations of hIL-1β were treated alone or co-treated with hIL-1RA (R&D systems) or with anti IL1 Ra-hyFc fusion protein for 6 hours. After that the media was removed and the cells were washed with PBS. After complete removal of PBS, luminescence was measured using Dual-luciferase reporter assay system (Promega, E1960) according to the manufacturer's instruction.

Figure 16:
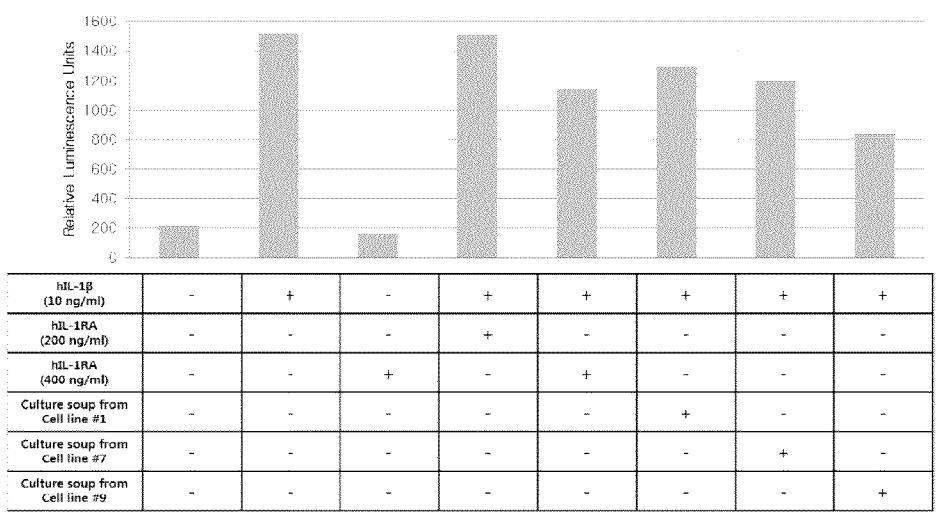
FIGS. 16 and 17 are results showing the inhibitory effect of IL-1 receptor antagonist-hybrid Fc fusion protein in NF-kB activation up on IL-1 stimulation according to one embodiment of the present disclosure.
Figure 17:
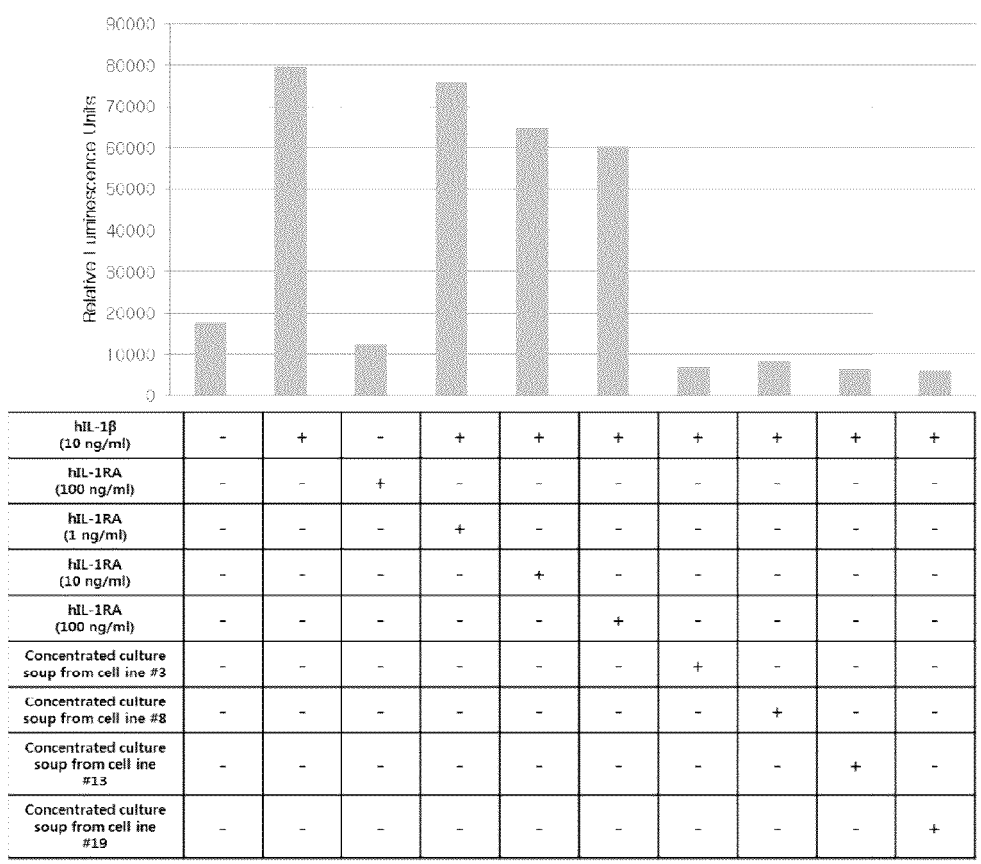

As shown in FIGS. 16 and 17, media from the cells that were not treated with any protein and treated with hILRA alone was used as a negative control, and media from the cells treated with hIL-1β was used as a positive control. FIG. 16 shows that the fusion protein obtained from various cell lines which express the fusion protein exerts comparable or better effect of blocking the signal transduction than that of commercially available hIL1RA. Also FIG. 17 shows that the blocking effect was increased by using the concentrated media derived from cells expressing the fusion protein.

(2) Comparison of Blocking Effect of Anakinra, hIL-1RI-Hybrid Fc Fusion Protein and the Present Fusion Protein on the Signal Transduction via hIL-1β

Commercially available anakinra protein or hIL-1RI hybrid Fc fusion protein which bind to hIL-1β and the present fusion protein was used to compare their effect on suppressing the transduction signaling via hIL-1β.

HeLa cells ($2\times10^4$) were seeded in each well of 48 well plate at 24 hours prior to transfection. Next day, the cells were co-transfected with a firefly luciferase plasmid having a NFkB binding site and a renilla luciferase plasmid having CMV promoter which is used to normalize the result. Three hours after the transfection, cells were replaced with fresh media and stabilized for 24 hours. The varying concentrations of hIL-1β were treated alone or co-treated with anakinra protein or with hIL-1RI hybrid Fc fusion protein which bind to hIL-1β or with the present fusion protein for 6 hours. After that the medium was removed and the cells were washed with PBS. After complete removal of PBS, the luminescence was measured using Dual-luciferase reporter assay system (Promega, E1960) as instructed.

Figure 18:
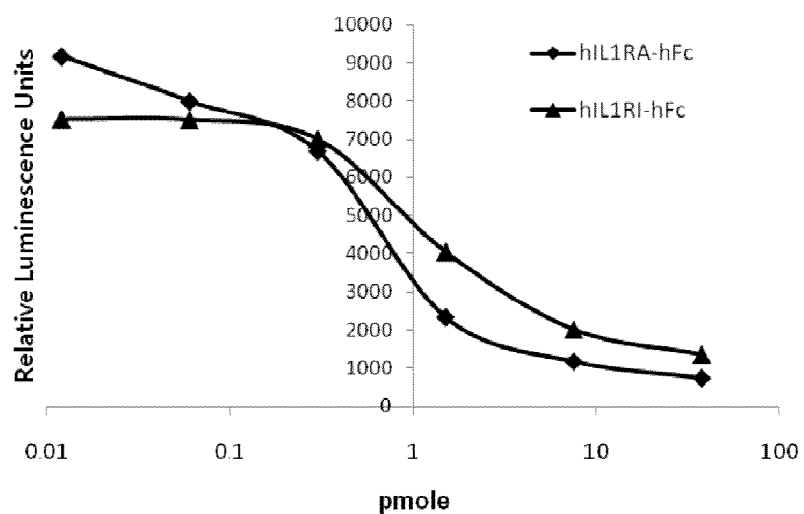
FIG. 18 is a result showing the inhibitory effect of IL-1 receptor antagonist-hybrid Fc fusion protein in NF-kB activation up on IL-1 stimulation according to one embodiment of the present disclosure.
Figure 19:
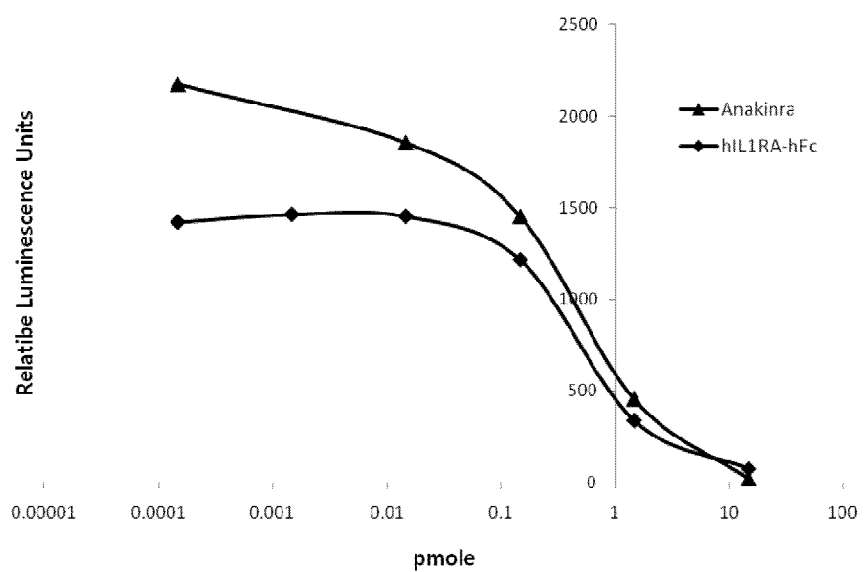
FIG. 19 is a result showing the inhibitory effect of IL-1 receptor antagonist-hybrid Fc fusion protein in NF-kB activation up on IL-1 stimulation according to one embodiment of the present disclosure.

As shown in FIGS. 18 and 19, the results indicate that the present fusion protein has better effect on blocking the signal transduction than that of hIL-1RI hybrid Fc control. Also FIG. 19 shows that the present fusion protein exerts a better blocking effect compared to that of commercially available hIL-1 RA in cells.

Example 10

Detection of IL-8 Using ELISA

The level of IL-8 was measured using ELISA to compare the effect of the present fusion protein on inhibiting IL-8 secretion with the effect of anakinra and hIL1RA fused to IgG1 Fc.

HeLa cells ($2\times10^4$) were seeded in each well of 48 well plate at 24 hours prior to transfection. Then the hIL-1β were treated alone or co-treated with anakinra or with hIL1RA fused to IgG1 Fc or with the present fusion protein at various concentrations for 24 hours. After the incubation, the media were collected and the amount of IL-8 was measured in each medium using Duoset ELISA development quantitation kit (R&D systems., Inc., DY208) according to the manufacturer's instruction. 100 µl of coating antibody diluted with coating buffer was added to each well of 96 well plate and the plate was incubated at RT. Then the plate was washed 3 times with TBST and 300 µl of blocking buffer containing 1% BSA was added to each well and the plate was incubated for 1 hour at RT. The plate was then washed 3 times with TBST and 100 µl of standard solution in two fold serial dilution from 500 pg/ml to 0 pg/ml or the diluted sample were added to each well and the plate was incubated for 2 hour at RT.

After the incubation, the plate was washed 3 times with TBST and 100 µl of biotin conjugated anti-hIL-8 detection antibody was added to each well and the plate was incubated for 2 hours. The plate was then washed 3 times with TBST and incubated with 100 µl of Streptavidin HRP conjugated antibody at a ratio of 1:200 for 20 min at RT. Then the plate was washed 3 times with TBST and 100 µl of TMB substrate was added to each well and incubated in the dark for 20 min at RT. The reaction was terminated by adding 50 µl of stop solution and the absorbance was measured in a plate reader at 450 nm. The concentration of IL-8 was calculated as ng/ml by multiplying the value obtained from ELISA by dilution factor.

Figure 20:
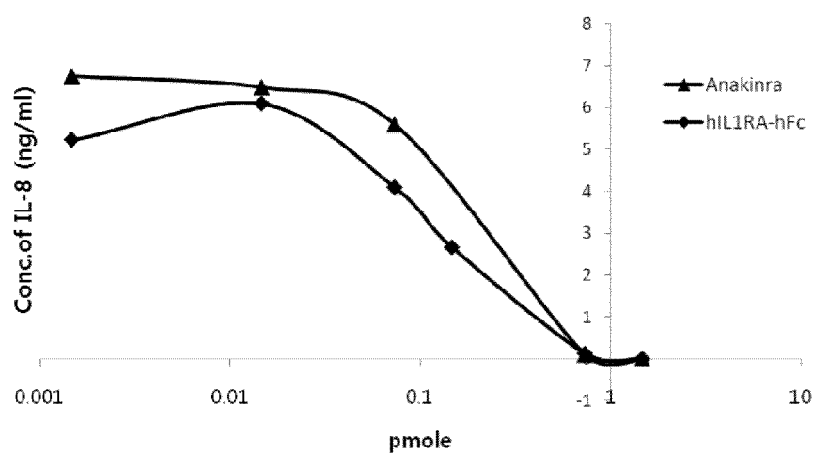
FIG. 20 is a result a result showing the inhibitory effect of IL-1 receptor antagonist-hybrid Fc fusion protein in production of Interleukin-8 up on IL-1 stimulation according to one embodiment of the present disclosure.
Figure 21:
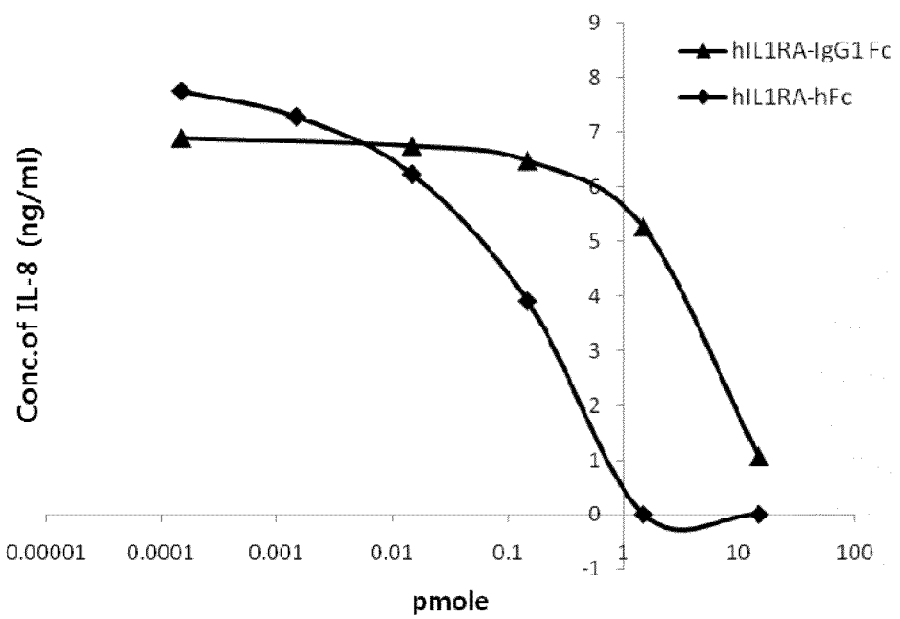
FIG. 21 is a result showing the inhibitory effect of IL-1 receptor antagonist-hybrid Fc fusion protein in production of Interleukin-8 up on IL-1 stimulation according to one embodiment of the present disclosure.

FIGS. 20 and 21 show that the present fusion protein has blocking effect of the IL-8 production, a proinflammatory cytokine, by blocking hIL-1beta in cells. Here anakinra and IL-1RA fused to IgG1 Fc were used for comparison.

As shown in FIG. 20, when co-treated with hIL-1beta the present fusion protein exerted a better blocking activity of IL-8 secretion than that of commercially available anakinra. Also FIG. 21 shows that the present fusion protein has better blocking activity than that of the IL-1RA fused to IgG1 Fc.

Example 11

Determination of the Effect of the Present Fusion Protein on Suppressing Arthritis Using Collagen-Induced Arthritis Mouse Model Six weeks old DBA-1 mouse was treated with 100 mg of bovine type II collagen (CII) and complete Freund's adjuvant (CFA) (Arthrogen-CIA, Redmond, Wash., USA) by subcutaneous injection into the part of the tail for inducing arthritis. After 2 weeks, 100 mg CII and incomplete Freund's adjuvant (DIFCO, Detroit, Mich.) were injected into the hind limb. To test the effect of anakinra and the present hIL1RA-hyFc fusion protein on progressing arthritis, from the second week after the first collagen injection, the mice was treated with various concentrations of anakinra or the present hIL1RA-hyFc fusion protein every other day for 4 weeks by peritoneal injection. To evaluation of the effect on arthritis two independent persons performed the evaluation 3 times a week for 7 weeks after the first injection on the four limbs. The evaluation was rated on a scale of 0-4 and the averaged values were used.

Figure 22:
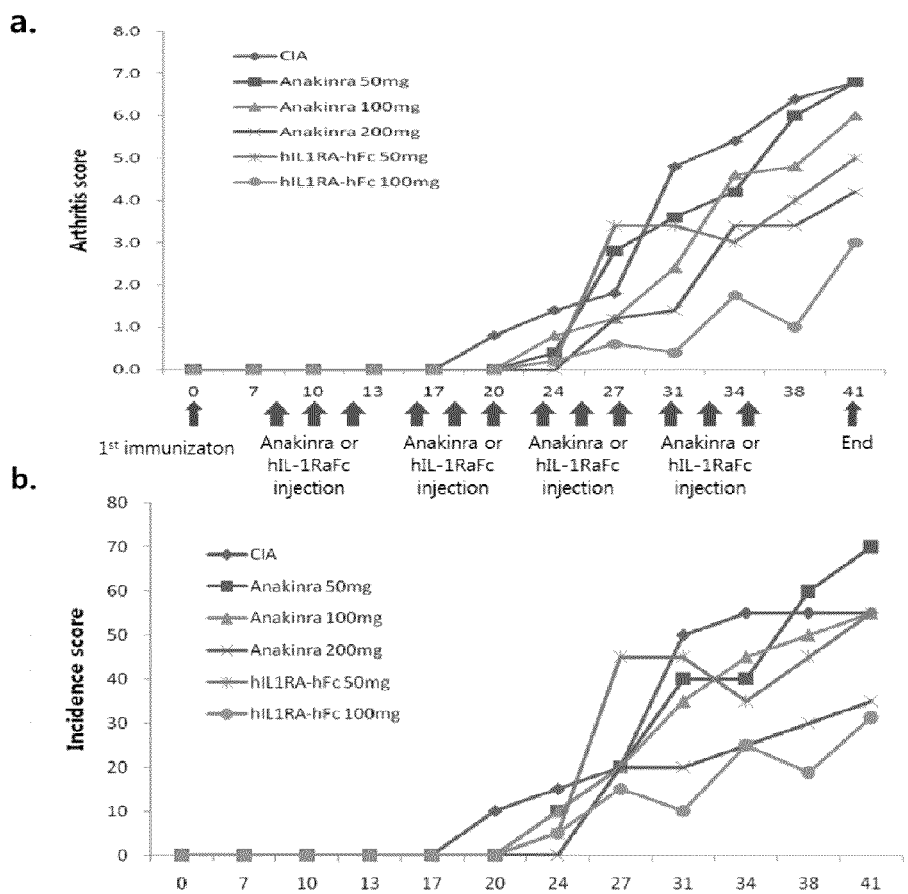
FIG. 22 is a result showing the therapeutic effect of IL-1 receptor antagonist-hybrid Fc fusion protein on the progress of collagen induced arthritis on various concentrations according to one embodiment of the present disclosure.

FIG. 22 shows the effect of the present fusion protein on the arthritis in a collagen induced arthritis mouse model. Here negative control mouse was not treated with the protein and the positive control mouse was treated with IL-1RA, anakinra.

As shown in FIGS. 22(*a*) and (*b*), the present fusion protein successfully suppressed the development of arthritis at the lower concentration than that of hIL-1RA.

The various singular/plural permutations may be expressly set forth herein for sake of clarity. Although a few embodiments of the present disclosure have been shown and described, it would be appreciated by those skilled in the art that changes may be made in this embodiment without departing from the principles and spirit of the invention, the scope of which is defined in the claims and their equivalents.

What is claimed is:

1. A fusion protein comprising a human IL-1 receptor antagonist linked to a human immunoglobulin hybrid Fc fragment, said fusion protein comprising the amino acid sequence of SEQ ID NO: 7.

2. A pharmaceutical composition comprising the fusion protein according to claim 1 and a pharmaceutically acceptable carrier.

3. A nucleic acid molecule encoding the fusion protein of claim 1 wherein the nucleic acid molecule comprises the nucleotide sequence represented by SEQ ID NO: 6.

4. A method of suppressing rheumatoid arthritis in a mammal in need thereof comprising administering the fusion protein of claim 1 to the mammal.

* * * * *